United States Patent [19]

Graham

[11] Patent Number: 5,246,458
[45] Date of Patent: Sep. 21, 1993

[54] ARTIFICIAL DISK

[76] Inventor: Donald V. Graham, 1340 Gulf Blvd. #11-C, Clearwater, Fla. 34630

[21] Appl. No.: 957,144

[22] Filed: Oct. 7, 1992

[51] Int. Cl.[5] .......................... A61F 2/44; A61F 5/04
[52] U.S. Cl. ...................................... 623/17; 606/61; 606/60; 606/86; 606/87
[58] Field of Search ............... 623/16, 17, 18; 606/60, 606/61, 69, 70, 71, 72, 79, 80, 86, 87, 96

[56] References Cited

U.S. PATENT DOCUMENTS

| | | | |
|---|---|---|---|
| 3,426,364 | 2/1969 | Lumb | 623/17 |
| 3,987,499 | 10/1976 | Scharbach et al. | 623/17 |
| 4,289,123 | 9/1981 | Dunn | 623/17 |
| 4,636,217 | 1/1987 | Ogilvie et al. | 623/17 |
| 4,759,766 | 7/1988 | Buettner-Janz et al. | 623/17 |
| 4,759,769 | 7/1988 | Hedman et al. | 623/17 |
| 4,874,389 | 10/1989 | Downey | 623/17 |
| 4,892,545 | 1/1990 | Day et al. | 623/17 |
| 4,932,975 | 6/1990 | Main et al. | 623/17 |
| 4,946,378 | 8/1990 | Hirayama et al. | 623/17 |
| 4,946,458 | 8/1990 | Harms et al. | 623/17 |
| 4,997,432 | 5/1991 | Keller | 623/17 |
| 5,071,437 | 12/1991 | Steffee | 623/17 |
| 5,123,926 | 6/1992 | Pisharodi | 623/17 |

Primary Examiner—David Isabella
Attorney, Agent, or Firm—Franklin J. Cona

[57] ABSTRACT

An artificial intervertebral disk for replacing a damaged human disk between two adjacent vertebrae in a human spinal column is disclosed. The invention comprises a pair of cylindrically shaped members in a vertical stacked relationship and a flexible spacer therebetween. The cylindrically shaped members are joined together in a ball and socket relationship which provides full rotational movement thereof. The flexible spacer therebetween provides the resilient compressive strength necessary to maintain the vertical separation of the adjacent vertebrae. The flexible resilient spacer completely surrounds the ball and socket portions of the cylindrically shaped members. Each cylindrically shaped member is fastened to the bone in the adjacent vertebrae with an arcuate plate and is secured with a fastener that engages the bone in the adjacent vertebrae and a threaded recess in the cylindrically shaped member. A cavity is routed out of the adjacent vertebrae by a routing guide tool and the invention is implanted in the patient by a special alignment and holding tool that allows the surgeon to drill through channels in the bone in the adjacent vertebrae in perfect alignment with threadable recesses in the cylindrically shaped members. An sized fastener is inserted through an aperture in the arcuate plate and engages the bone material and a threaded portion the recess in the cylindrically shaped member.

20 Claims, 7 Drawing Sheets

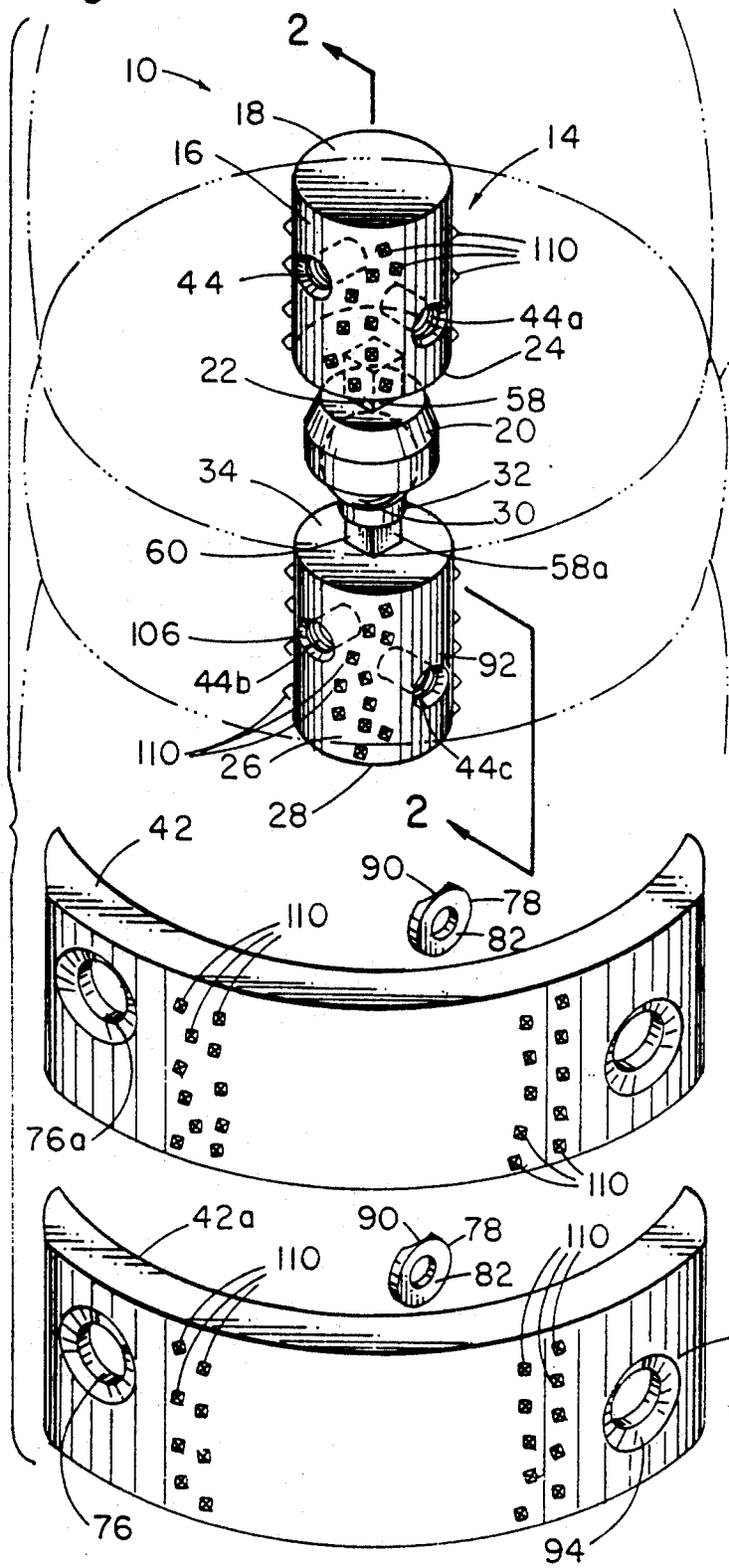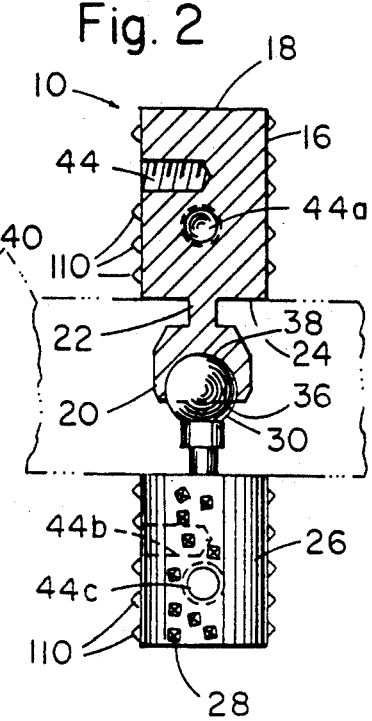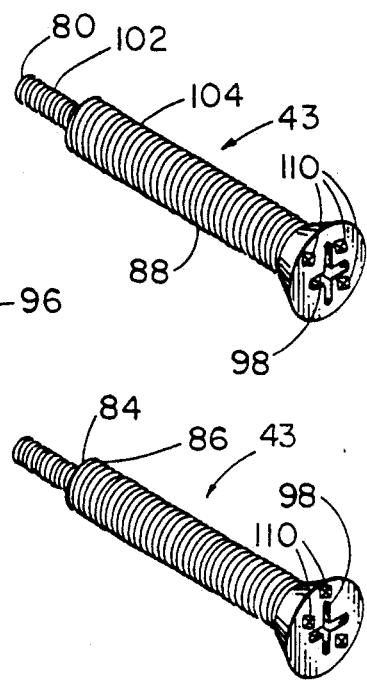

ARTIFICIAL DISK

BACKGROUND OF THE INVENTION

1. Field of the Invention

The present invention relates to an artificial intervertebral disk to replace a damaged human disk between two adjacent vertebrae in a human spinal column. More particularly, the invention relates to an artificial intervertebral disk which is secured in place between two adjacent vertebrae and maintains the full range of rotational motion that the natural disk provided.

2. Description of the Background Art

Throughout the United States steps are being taken artificial intervertebral disks. A common curse of humankind is a ruptured or herniated disk. The function of the human disk is to maintain separation between the adjacent vertebrae comprising the spinal column. A human spinal column has 5 vertebrae in the lumbar region and seven vertebrae in the cervical region and 12 vertebrae in the thoracic region. The lumbar region is commonly referred to as the lower back and the cervical region is commonly referred to as the neck. The thoracic region is in the middle of the spinal column. The spinal column is the primary structural element of the human skeleton. It is required to carry the compressive load of the upper portion of the body and transmit that load to the lower portion of the body. Consequently, it must have the compressive structural strength needed to perform that role over millions of cycles. Also, the spinal column must support the body under the normal human activities such as bending, turning, stooping over and engaging in various forms of exercise. To accommodate this requirement, the spinal column must be capable of rotational twisting without breaking. The dual role is accommodated by the interpositioning of a human disk between the adjacent vertebrae in the lumbar region and the cervical region and the thoracic region. The function of the human disk is to provide the compressive strength necessary to avoid having the adjacent vertebrae come in contact with each other. For example, the conventional surgical approach for a ruptured cervical disk is to remove the damaged cervical disk and fuse the space now developed between the adjacent vertebrae with a bone graft. Repair plates for anterior cervical fusion are known in the art. For example, a "caspar" repair plate is produced by the Aesculap Corporation of Burlingame Calif. It is disclosed under U.S. Pat. No. 4,503,848. Anterior cervical fusion has the disadvantage of reducing the range of rotational motion, due to the joining of the adjacent vertebrae. Over time, the range of motion reduction can be significant if more than one fusion is performed, particularly in the cervical region. Furthermore, it causes degeneration of the disk spaces above and below the levels of fusion.

Many artificial disk have been developed to replace a damaged human disk. However, none are completely satisfactory.

U.S. Pat. No. 4,874,389 issued to Downey discloses a replacement disk having two interengaged loops surrounded by an elastomeric body.

U.S. Pat. No. 4,946,378 issued to Hirayama et al. discloses an artificial intervertebral disk having a pair of end bodies and an intermediate elastic material.

U.S. Pat. No. 4,759,769 issued to Hedman et al. discloses an artificial disk having a hinged upper piece and a hinged lower piece with a coil spring therebetween.

U.S. Pat. No. 4,997,432 issued to Keller discloses an intervertebral disk having stop plates with two projections and a sliding core held between the stop plates.

U.S. Pat. No. 3,987,499 issued to Scharbach et al. discloses an implant for a hip bone having an upper and lower piece with a pin securing the upper and lower pieces.

U.S. Pat. No. 4,759,766 issued to Buettner-Janz et al. discloses an intervertebral disk having an upper and lower plate with an intermediate plate therebetween.

U.S. Pat. No. 4,932,975 issued to Main et al. discloses a prosthesis having a vertical body with a suspension medium surrounding a suspension plate.

U.S. Pat. No. 5,123,926 issued to Pisharodi discloses an artificial disk having a plurality of spring loaded cups positioned within a prosthesis for urging the implant to conform to the space between the adjacent vertebrae.

U.S. Pat. No. 5,071,437 issued to Steffee discloses a spinal disk prosthesis having an upper and lower plate with an elastomeric core sandwiched between the upper and lower plate.

U.S. Pat. No. 4,636,217 issued to Ogilvie et al. discloses a prosthetic implant held in place by screws in the adjacent vertebrae.

None of these previous efforts, however, provide the benefits intended with the present invention. Additionally, prior techniques do not suggest, the present inventive combination of component elements as disclosed and claimed herein. The present invention achieves its intended purposes, objectives and advantages over the prior art devices through a new, useful and unobvious combination of component elements, which is simple to use, with the utilization of a minimum number of functioning parts, at a reasonable cost to manufacture, assemble, test and by employing only readily available material.

Therefore, it is an object of the present invention to provide a artificial intervertebral disk which can be used in place of the damaged human disk and maintain the full range of motion heretofore enjoyed by the person.

It is a further object of the invention to provide an artificial intervertebral disk to maintain the full separation distance between the adjacent vertebrae heretofore enjoyed by the person.

It is a still further object of the invention to provide an artificial intervertebral disk that is biochemically stable and biocompatable with the human skeletal system and tissue.

It is another object of the invention to provide an artificial intervertebral disk that will encourage rapid adherence to the surrounding bone and tissue after the implantation.

It is still another object of the invention to provide an artificial intervertebral disk that can be implanted in the person with standard surgical drills and drill bits.

It is another object of the invention to provide an alignment and holding tool to enable the surgeon to implant the artificial intervertebral disk with consistent alignment of all the components of the invention.

It is another object of the invention to provide an artificial intervertebral disk that is maintained in the same relative position in the spinal column by means of fasteners securely engaged to the bone material and to the threaded recesses in the cylindrically shaped members.

It is a final object of the invention is to provide an artificial intervertebral disk that can be implanted in a patient with their respective ball and socket members oriented in a upper and lower relationship that has equally satisfactory outcomes either when the ball member is oriented above the socket member or when the respective positions are reversed.

Although there have been many inventions related to an artificial disk, none of the inventions have become sufficiently compact, low cost and reliable enough to become commonly used. The present invention meets the requirements of a simplified design, compact size, low initial cost, ease of implantation and maintainability, and minimal amount of training to successfully employ the invention. The artificial disk of the present invention is easy to manufacture, maintenance free, and biochemically stable when implanted in the human spinal column.

The foregoing has outlined some of the more pertinent objects of the invention. These objects should be construed to be merely illustrative of some of the more prominent features and applications of the intended invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description of the preferred embodiments in addition to the scope of the invention defined by the claims taken in conjunction with the accompanying drawings.

SUMMARY OF THE INVENTION

The invention is defined by the appended claims with the specific embodiment shown in the attached drawings. For the purpose of summarizing the invention, the invention may be incorporated into an artificial intervertebral disk for replacing a damaged human disk for preserving the full functionality of the spinal column after the operation is completed.

More particularly, the invention comprises a pair of cylindrically shaped members in a vertical orientation and a flexible spacer therebetween. The cylindrically shaped members are joined in a ball and socket relationship to provide the full range of rotational motion that the damaged disk heretofore gave the person. The ball and socket portion of the invention is completely surrounded by the flexible spacer and occupies the space that the damaged human disk occupied. The flexible spacer provides the compressive strength necessary to maintain separation between a pair of adjacent vertebrae.

Each cylindrically shaped member is secured in the spinal column with arcuate shaped plates and fasteners. The fasteners have a multi diameter shank which provides for secure engagement with the cancellous bone material and machine thread engagement with a recess located in the respective cylindrically shaped member.

A specially designed alignment and holding tool allows the surgeon to drill thru channels in the adjacent vertebrae in perfect alignment with the threaded recesses in the cylindrically shaped members. The alignment and holding tool maintains a constant vertical distance between a fixturing member of the alignment and holding tool and a tubular drill guide member equal to a distance from a mid-portion of a stem of each cylindrically shaped member to the respective threaded recess in the cylindrically shaped member. Thus, the chance for misalignment of the drilled channel in the bone is eliminated. Also, a depth gage is used to determine the proper size fastener.

An arcuate cover plate is then put over each vertebrae and properly sized fasteners are threaded into the channels in the adjacent vertebrae and into the threaded recesses in the cylindrically shaped members. The invention provides a secure replacement for a damaged human disk and maintains the full range of functionality that the person enjoyed prior to the human disk becoming damaged.

The exterior surfaces of the cylindrically shaped members, the arcuate plates, the fasteners and the washers all have a surface adapted to encourage bone growth adherence to the surrounding bone and tissue after the operation is completed. The invention can be installed with the cylindrically shaped member having a ball in the upper position and the cylindrically shaped member having a socket in the lower position. Equally satisfactory outcomes are achieved when the respective positions of the cylindrically shaped members are reversed.

The invention is implanted in the patient by first exposing the anterior portion of the spinal column and removing the damaged disk from between the two adjacent vertebrae. A cavity sufficiently sized to accept the invention is routed out of the two adjacent vertebrae by the surgeon using a specially designed routing guide and a conventional surgical drill. The surgeon then implants the artificial disk in the cavity and fixtures the disk to maintain a steady motionless state. The alignment and holding tool maintains the proper spacing with respect to the threaded recesses in the cylindrically shaped members. Then, the surgeon drills a plurality of through channels in the bone in the adjacent vertebrae with a conventional prior art surgical drill and surgical drill bits. Typically, the drill bits have a collet to prevent over drilling by the surgeon. The surgeon measures the depth of each channel drilled through the bone using a conventional depth gage, and then he or she selects a proper length screw to thread through the channel and engage the threaded recess in the cylindrically shaped member.

Then the surgeon packs the cavity with a cortico cancellous bone graft removed from another portion of the patients, body preferably from the iliac crest. The alignment and holding tool is then removed and an arcuate plate is placed over one of the adjacent vertebrae. The previously selected proper length fastener is screwed into the interior wall of the channel thru a lockwasher and finally into the threaded recess in the cylindrically shaped member. Usually, about four screws are required. When the screws are securely engaged to the interior walls of the channel and lockably threaded in the recesses in the cylindrically shaped members, the operation is completed, and the surgeon closes up the anterior portion of the spinal column.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent structures do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 1 is a perspective of the invention showing the cylindrically shaped members in the stacked vertical relationship and the flexible spacer therebetween in phantom completely surrounding the ball and socket portions of the respective cylindrically shaped member. FIG. 1 also shows the exploded assembly perspective of the arcuate plates, the multi-diameter fasteners and the lock washers prior to complete assembly in the cavity in the adjacent vertebrae of the spinal column.

FIG. 2 is a sectional elevation view taken along lines 2—2 in FIG. 1 showing the rotational relationship between the ball and socket components of the respective cylindrically shaped member.

FIG. 4 shows the placement of the cylindrically shaped member in the cavity and the packing of the cavity with the cortico cancellous bone graft. Additionally, FIG. 4 shows the attachment of the arcuate plate to the cylindrically shaped member with the use of the multi-diameter fastener and a lock washer.

Similar reference characters refer to similar parts throughout the several views of the drawings.

DETAILED DESCRIPTION OF THE PREFERRED EMBODIMENT

Figure 3:
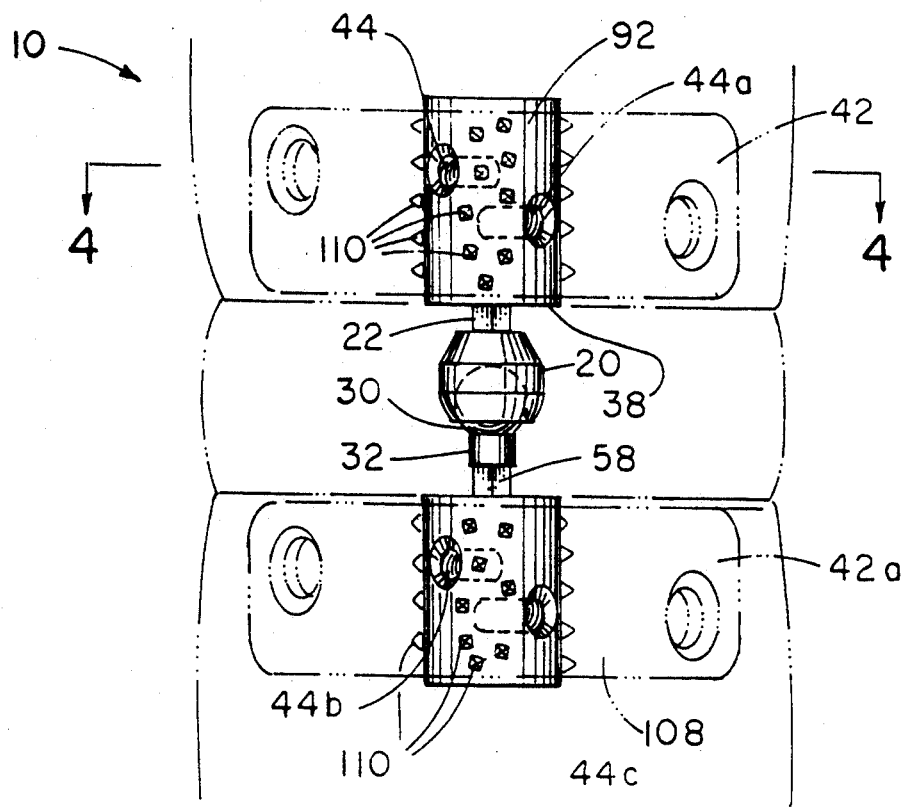
FIG. 3 is a side elevation view of the invention in the patient showing the alignment of the aperture in the arcuate shaped plates with the threaded recesses in the cylindrically shaped members. The flexible spacer and the adjacent vertebrae are shown in phantom to disclose the squared mid-portion of the stem for engagement with the fixturing member of the alignment and holding tool.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of structures and the combination and arrangement of parts may be resorted to without departing from the spirit and scope of the invention.

Referring to FIG. 1, the invention comprises an artificial disk 10 and a plurality of alignment and holding tools 12, 12a to allow a surgeon to replace a damaged human disk between two adjacent vertebrae in a spinal column of a patient. The artificial disk 10 further comprises a pair of cylindrically shaped members 14 in a mated, stacked, vertical relationship. The upper member 16 has a top end 18 and a spherical socket 20 depending downwardly from a stem 22 on a bottom end 24. The lower member 26 has a bottom end 28 and a spherical ball 30 depending upwardly from another stem 32 on a top end 34. An interior surface 36 of the spherical socket 20 engages an exterior surface 38 of the spherical ball 30 in a rotational, mated relationship. The cylindrically shaped members 14 can be fabricated from a bio-compatible rigid material, for example stainless steel or a titanium alloy, preferably stainless steel.

A flexible spacer 40 completely surrounds the socket 20 and the spherical ball 30 and their respective stems 22, 32 to maintain the separation distance between the adjacent vertebrae, as best seen in FIG. 2. The flexible spacer 40 can be fabricated from a biocompatible resilient material, for example a silicone elastomer or silicone rubber, preferably a silicone elastomer.

A plurality of arcuate plates 42 and threaded fasteners 43 secure the upper member 16 and the lower member 26 to the adjacent vertebrae.

Each cylindrically shaped member 16, 26 has a plurality of threaded recesses 44, 44a, 44b, 44c, each recess 44, 44a, 44b, 44c being adapted to receive one of a plurality of the threaded fasteners 43.

Figure 5:
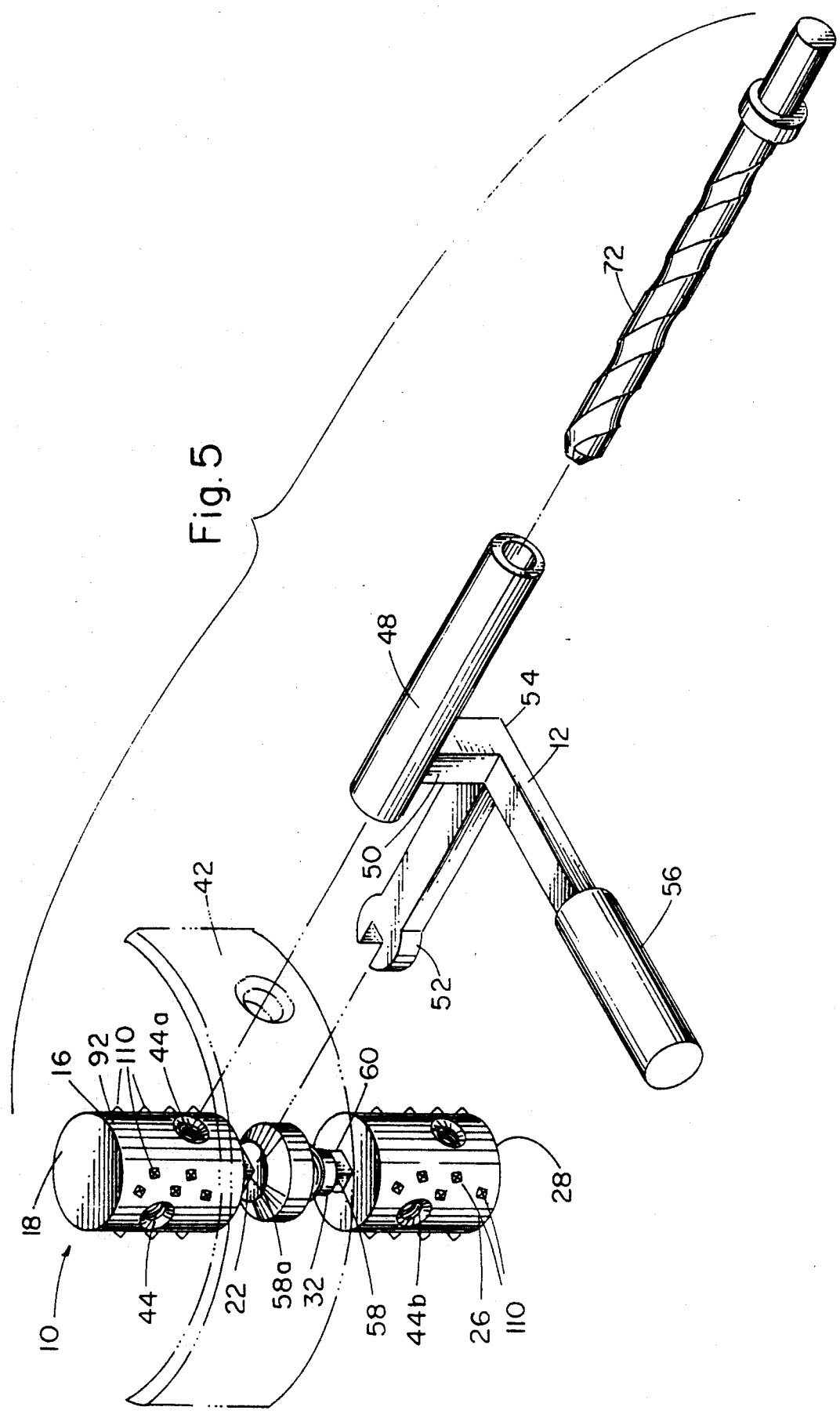
FIG. 5 is a perspective view of the alignment and holding tool showing the fixturing member, the alignment drill bit guide and the handle therebetween for the surgeon to grasp. The surgeon deploys the fixturing member on the squared portion of the mid-section of the stem prior to drilling thru channels in the bone that align with the threaded recesses in the cylindrically shaped members. The surgeon uses a non-illustrated drill with a drill bit fitted with a collet to prevent overdrilling.

As best seen in FIG. 5, each alignment tool 12 has an open ended tube 48 on a first end 50, a fixturing member 52 on the second end 54, and a handle 56 therebetween for the surgeon to grasp when in use and operation. The open ended tube 48 and the fixturing member 52 are aligned coaxially to allow the surgeon to place the fixturing member 52 on a middle portion 58 of the respective stem 22, 32 of the spherical socket 20 or spherical ball 30. The middle portion 58 of each stem 22, 32 has a square cross section 60 in the preferred embodiment, however a hexagonal or octagonal cross section is also feasible. The alignment and holding tool 12 can be made from a surgical grade of steel, preferably stainless steel.

The open ended tube 48 is disposed from the fixturing member 52 at a vertical distance approximately equal to the vertical distance from the middle portion 58 of the respective stem 22, 32 to one of the plurality of threaded recesses 44 in each one of the paired cylindrically shaped members 14. The open ended tube 48 and the fixturing member 52 of each alignment and holding tool 12, 12a have a coplanar alignment and the handle 56 is oriented transversely to the open ended tube 48 and the fixturing member 52.

Thus, for example, when the fixturing member 52 is securely engaged on the middle section 58 of the stem 32 of the cylindrically shaped member 26 with the spherical ball 30, the open ended tube 48 is in axial coalignment with one of the recesses 44 in the cylindrically shaped member 26. Likewise, when the fixturing member 52 is securely engaged on the middle portion 58a of the stem 22 of the cylindrically shaped member 16 with the spherical socket 20, the open ended tube 48 is in axial coalignment with one of the recesses 44a in the cylindrically shaped member 16.

The major advantage of the artificial disk invention is to preserve the normal function and range of rotational movement of the spinal column, and in particular the cervical spine. The majority of movement within the cervical spine occurs at the top two vertebrae, C1 and C2. Approximately 50of the motion in the neck occurs at these two disks, and the remaining 50% is spread over the remaining five (5) disks of the cervical region. Therefore, the remaining five (5) disks each supply approximately 10% of the movement of the neck. The current surgical procedure of anterior cervical fusion results in approximately 10% loss per level of fusion or disk removal. Frequently over time, these fusions are performed at multiple levels. This results in a large degeneration of the range of movement and a significant loss of function in the cervical spine. After the fusion is performed there is a high risk of degenerative arthritis and disk herniation occurring at the disk above and below the location where the disk has been removed.

The artificial disk 10 meets the needs of the patient, particularly when being implanted in the cervical region of the spinal column. The flexible spacer 40 provides the compressive strength necessary to keep the two adjacent vertebrae from contacting each other. Also, since each arcuate plate 42 is attached to an individual vertebrae, the patient retains the full range of rotational motion in the spinal column after the operation, as opposed to a reduction in the range of motion when anterior cervical fusion linking the two adjacent vertebrae is used.

The artificial disk 10 can also be implanted in the lumbar region of the spine. The compressive strength of the flexible spacer 40 is more important in the lumbar region than the loss of rotational movement around the lower lumbar spinal axis.

In use and operation, the surgeon prepares the patient to receive the artificial disk 10 by first exposing the anterior portion of the spinal column and removing the damaged human disk from between the pair of two adjacent vertebrae. The above step is known in the art and is achieved with prior art instruments. Accordingly, no further discussion is deemed necessary concerning the above surgical step.

Figure 4:
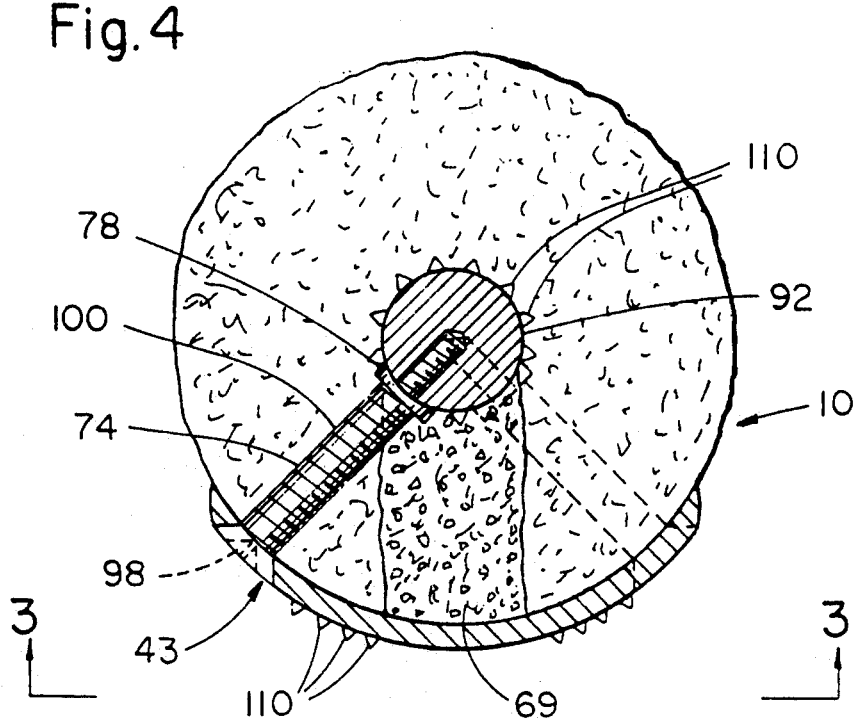
FIG. 4 is a cross-sectional plan view taken along lines 3—3 in FIG. 3.
Figure 6:
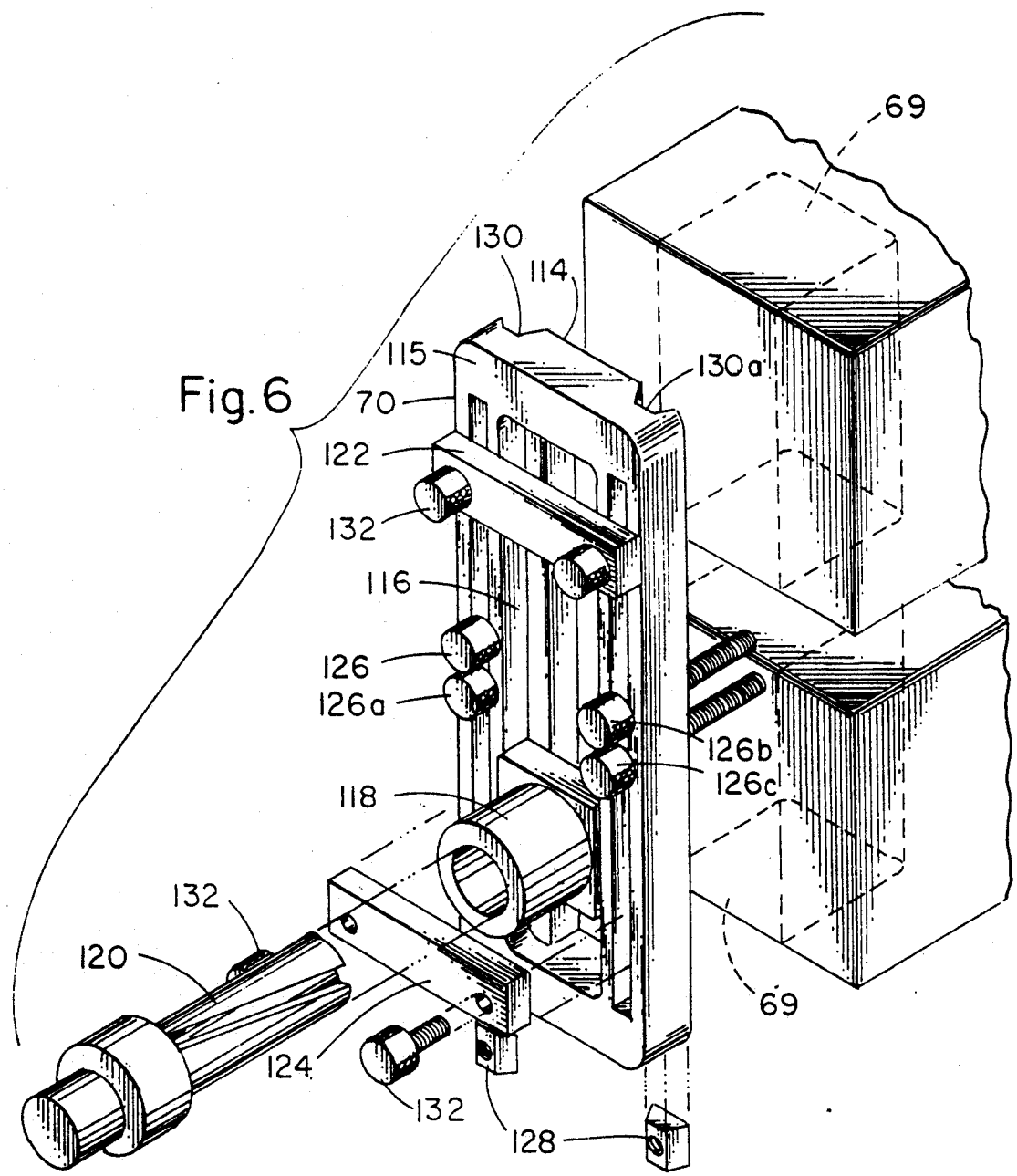
FIG. 6 is a perspective of the routing guide tool showing the guide prior to the temporarily attachment to the adjacent vertebrae and the routing bit aligned with the router slide.

Then a cavity 69 is routed out of the two adjacent vertebrae sufficiently sized to accept the artificial disk 10 using a routing guide 70 to insure proper vertical alignment within the spinal column as best seen in FIG. 6. In the next step, the surgeon implants the artificial disk 10 in the previously prepared cavity 69 and fixtures the artificial disk 10 with the alignment and holding tool 12, 12a. The alignment and holding tool 12, 12a maintains the paired, cylindrically shaped members 14 in a motionless, fixed relationship to the two adjacent vertebrae while a non-illustrated surgical drill with a drill bit 72 is used to drill a plurality of channels 74, through the bone in the two adjacent vertebrae as best seen in FIG. 4. Surgical drills are known in the art and no further discussion is deemed necessary concerning the surgical drill used in operating rooms.

The axial coalignment of the open ended tube 48 and one of the recesses 44 urges the surgeon to drill the first channel 74 in the bone in the adjacent vertebrae that is in perfect axial alignment with one of the recesses 44 in the cylindrically shaped member 16, 26. Since the plurality of recesses 44 in each cylindrically shaped member 16, 26 are disposed vertically from each other, the second alignment and fixturing tool 12a is required for urging coalignment of the second channel 74a in the bone of the adjacent vertebrae with the second recess 44a in the cylindrically shaped member 16, 26.

After the required number of channels 74 have been drilled through the bone the surgeon measures the depth of the channel 74 using a non-illustrated depth gage in order to select the properly sized threaded fastener 43 for later use in the operation. The fastener 43 should be about fifteen (15) millimeters in length in most cases. The cavity 69 is packed with a cortico cancellous bone graft taken from another part of the patients' body. The preferred bone graft is autogenous, or from the patient. However, an autologous graft from another person is an alternative embodiment. Then, the arcuate plate 42 is fitted over one of the adjacent vertebrae. The arcuate plate 42 has a plurality of apertures 76, 76a, each sized to urge passage of the threaded fastener 43 through the arcuate plate 42. A washer 78 is slidingly engaged over a distal end 80 of the threaded fastener 43 after the distal end 80 traverses through the channel 74 in the bone, but before the distal end 80 threadably engages one of the recesses 44 in the cylindrically shaped member 16, 26. The washer 78 has a flattened first surface 82 for securely contacting a transverse section 84 of a mid-section 86 of a shank 88 of the threaded fastener 43, and an arcuate second surface 90 for continuous lockable engagement with an outer periphery 92 of the cylindrically shaped member 16, 26.

Each arcuate plate 42 has a section 94 having an outer surface 96 surrounding each aperture 76, the section 94 having an inward slope towards the aperture 76 to urge coalignment of a slotted head 98 of the fastener 43 with the outer surface 96 of the arcuate plate 42 after the threaded fastener 43 is fully threadably engaged with an interior wall 100 of the channel 74 and the threadable portion of the recess 44.

The distal end 80 has a diameter smaller than the diameter of the mid-section 86 of the threaded fastener 43. The smaller diameter of the distal end 80 of the shank 88 is for urging undisturbed passage of the distal end 80 through the channel 74 drilled in the bone. The diameter of the mid-section 86 is sized to threadably engage an interior wall 100 of the channel 74 in the bone and secure each arcuate plate 42 to an outer surface of the bone. A machine thread 102 on the distal end 80 of the shank 88 has the same pitch as a cancellous thread 104 on the mid-section 86 for urging balanced, synchronized tightening of the cylindrically shaped member 16, 26 with the arcuate plate 42 as the threaded fastener 43 traverses the channel 74.

After the distal end 80 of the shank 88 passes through the channel 74, the distal end 80 engages one of the recesses 44 in the cylindrically shaped member 16, 26 for threadable engagement therein. An area 106 on the outer periphery 92 of the cylindrically shaped member 16, 26 is sloped inwardly toward the recess 44 to urge the distal end 80 to funnel toward the recess 44 if for any reason, the threaded fastener 43 is misaligned with the recess 44. The slotted head 98 of the threaded fastener 43 is available in common configurations, for example, a slotted configuration or a phillips head cross-slot configuration. Other configurations can also be employed successfully.

The cylindrically shaped members 14 and the arcuate plates 42, 42a have an outer surface 108 with a plurality of protuberances 110 for urging bone growth adherence to the surrounding human tissue and bone. Likewise, the threaded fasteners 43 and washers 78 have a the surrounding vertebral bone.

The drawings disclose the spherical socket member 16 in the upper position of the stacked vertical relationship and the spherical ball member 26 in the lower position. It should be understood that the invention can be implanted in a patient with their respective positions reversed with an equally satisfactory outcome.

Figure 8:
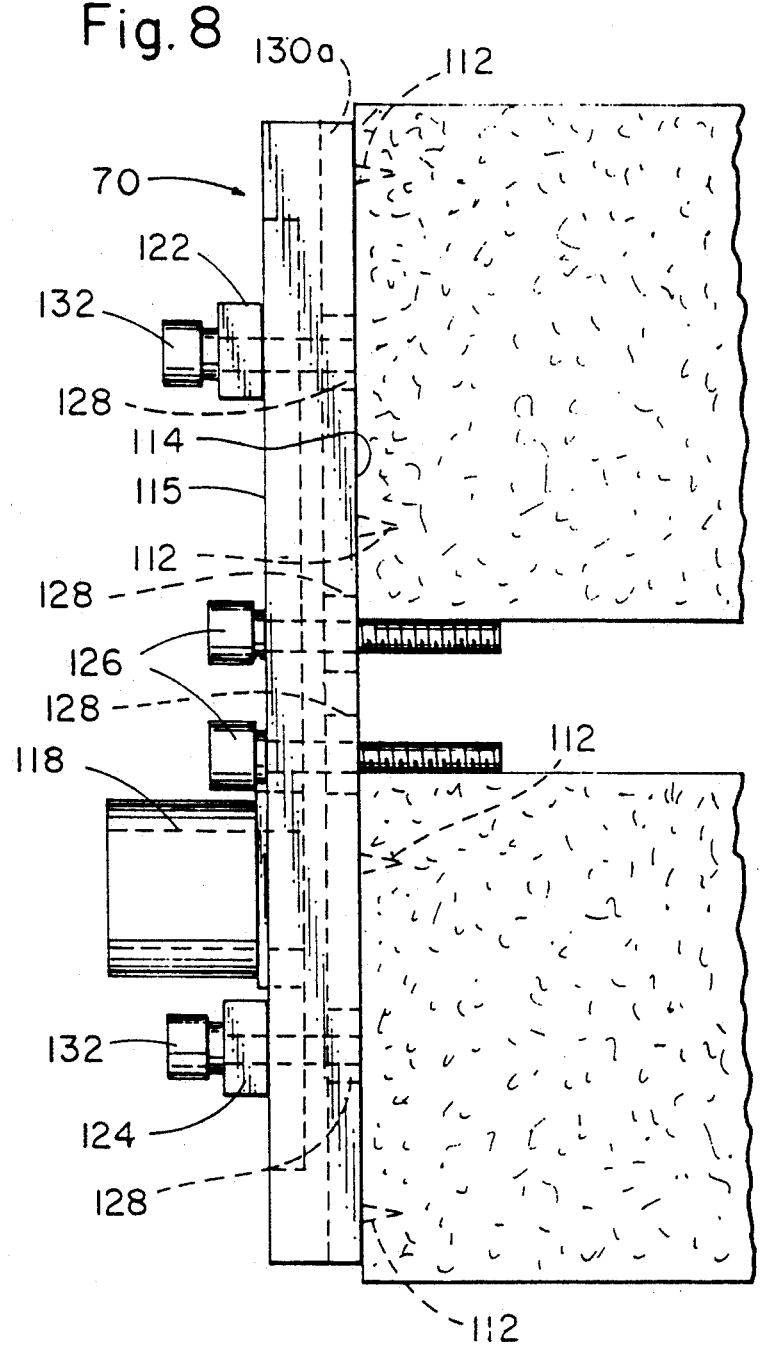
FIG. 8 is a side elevation view showing the routing guide temporarily secured to the adjacent vertebrae and the adjusting screws engaged with the adjacent vertebrae for maintaining the desired spacing.
Figure 9:
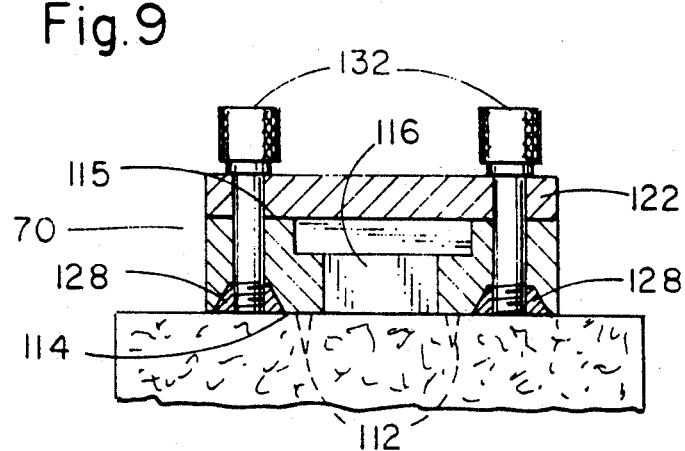
FIG. 9 is a cross sectional view taken along lines 9—9 of FIG. 7 showing the upper end stop with the adjusting screws and sliding nuts.
Figure 10:
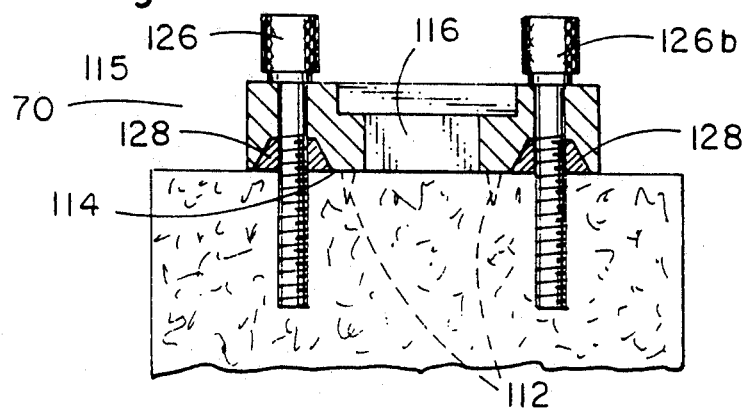
FIG. 10 is a cross sectional view taken along lines 10—10 of FIG. 7 showing the adjusting screws positioned to maintain the desired spacing between the adjacent vertebrae.
Figure 11:
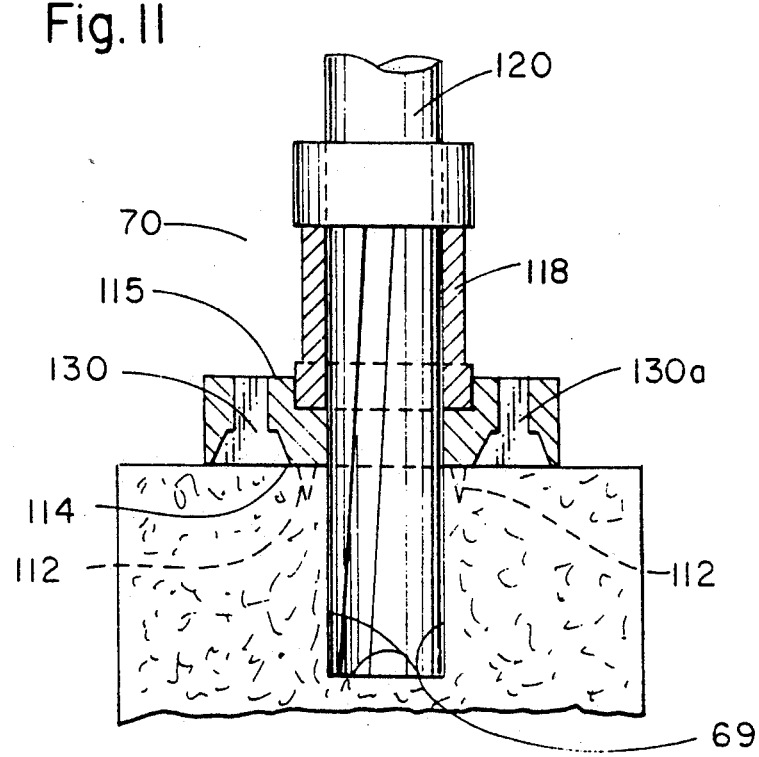
FIG. 11 is a cross sectional view taken along lines 11—11 of FIG. 7 showing the router slide being engaged with the router bit and routing out a cavity in the adjacent vertebrae.

As best seen in FIG. 8, the router guide 70 is temporarily attached to the two adjacent vertebrae with a plurality of minispikes 112 that project from a first surface 114 of the router guide 70. The router guide 70 has a second surface 115 with a vertically oriented rectangular slot 116 housing a slidable router bit aperture 118. As best seen in FIG. 11, the slidable router bit aperture 118 is adapted to move in a vertical direction and is further adapted to urge passage of a router bit 120 through the slidable router bit aperture 118 to routably engage the adjacent vertebrae and prepare the cavity 69 for reception of the artificial disk 10.

The router guide 70 has a upper stop 122, a lower stop 124 and a plurality of spacer screws 126, 126a, 126b, 126c therebetween. Each spacer screw 126 is adapted to threadably engage one of a plurality of slidable locknuts 128 located in a pair of channels 130, 130a in the router guide 70. The spacer screws 126, 126a, 126b, 126c are positioned to maintain the vertical spacing between the adjacent vertebrae after the damaged human disk has been removed, but before the artificial disk 10 has been implanted in the cavity 69 in the two adjacent vertebrae.

Figure 7:
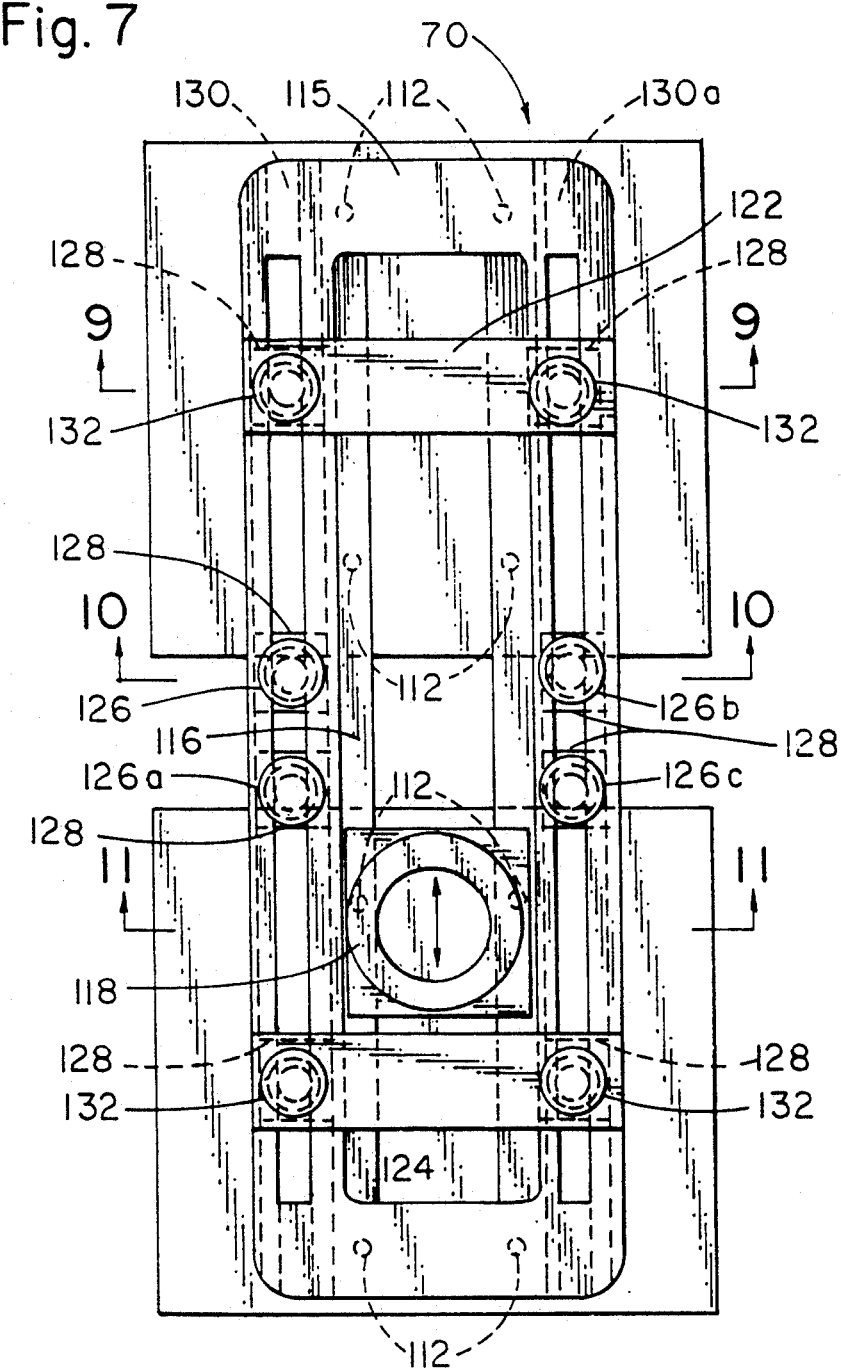
FIG. 7 is a front elevation view of the routing guide tool showing the router slide and the upper and lower end stops and the adjusting screws for maintaining the proper spacing between the adjacent vertebrae.

The upper stop 122 and lower stop 124 each have a plurality of slidable fasteners 132. Each slidable fastener 132 is adapted to engage one of the plurality of slidable locknuts 128 in the channels 130 for adjustably limiting the travel of the slidable router bit aperture 118 in the vertical slot 116 as best seen in FIGS. 6 & 7.

Now that the invention has been described,
What is claimed is:

1. An artificial intervertebral disk system for replacing a damaged human disk between two adjacent vertebrae in a spinal column and preserving the full range of motion and functionality of the spinal column comprising in combination;

paired cylindrically shaped members in a vertical, stacked, mated relationship and a flexible spacer therebetween, the paired cylindrically shaped members having an upper member having a top end and a bottom end having a downwardly depending stem with a spherical socket on a distal end thereof and further having a lower member having a bottom end and a top end having an upwardly depending stem with a spherical ball on a distal end thereof adapted for rotational mating with the spherical socket, the flexible spacer completely surrounding the spherical socket and the spherical ball for maintaining the separation distance between the adjacent vertebrae and preserving the full functionality of the spinal column;

a plurality of arcuate plates for urging securement of the paired cylindrically shaped members to the two adjacent vertebrae;

a plurality of fasteners for threadably attaching the artificial disk and the plurality of arcuate plates through the two adjacent vertebrae on the spinal column;

fixture means to hold the paired cylindrically shaped members in a fixed position for urging drilling of a plurality of channels through the two adjacent vertebrae for allowing threadable engagement of each one of the plurality of fasteners with the adjacent vertebrae; and second fixture means for temporarily holding the adjacent vertebrae in a steady motionless state for urging routing of a cavity in the adjacent vertebrae sufficiently sized to accept the paired cylindrically shaped members.

2. An artificial intervertebral disk system as recited in claim 1 wherein the upper member further includes a plurality of recesses, each recess being threadably adapted to receive one of the fasteners.

3. An artificial intervertebral disk system as recited in claim 1 wherein the lower member further includes a second plurality of recesses, each recess being threadably adapted to receive one of the fasteners.

4. An artificial intervertebral disk system as recited in claim 1 wherein the paired cylindrically shaped members are made from stainless steel.

5. An artificial intervertebral disk system as recited in claim 1 wherein the paired cylindrically shaped members are made from a titanium alloy.

6. An artificial intervertebral disk system as recited in claim 1 wherein the flexible spacer is made from a silicone elastomer.

7. An artificial intervertebral disk system as recited in claim 1 wherein the flexible spacer is made from a silicone rubber.

8. An artificial intervertebral disk system as recited in claim 1 wherein the fixture means further includes a plurality of alignment and holding tools for fixturing the paired cylindrically paired shaped members in a steady, fixed relationship to the two adjacent vertebrae for urging drilling of the plurality of channels in the two adjacent vertebrae, each channel being in a coaxial alignment with one of the recesses threadably adapted to receive one of the fasteners.

9. An artificial intervertebral disk system as recited in claim 1 wherein each arcuate plate further includes a plurality of apertures, each aperture for urging communication between one of the threadable recesses and one of the fasteners.

10. An artificial intervertebral disk system as recited in claim 8 wherein the alignment and holding tool further includes a open-ended tube on an end for urging coaxial alignment between one of the apertures on the arcuate plate and one of the threaded recesses, a fixturing member on another end for securely engaging a middle portion of the stem of the ball or socket member for urging motionless alignment of the ball and socket with the two adjacent vertebrae, and a handle therebetween for a surgeon to grasp.

11. An artificial intervertebral disk system as recited in claim 10 wherein the open-ended tube and the fixturing member of the alignment and holding tool are coplanar and the handle is disposed transversely to the open-ended tube and the fixturing member.

12. An artificial intervertebral disk system as recited in claim 10 wherein the alignment and holding tool is fabricated from a surgical quality stainless steel.

13. An artificial intervertebral disk system as recited in claim 1 wherein each fastener further has a slotted head on a first end and a shank with a machine thread on a distal end for threadably mating to one of the threadable recesses in the cylindrically shaped member, and a middle portion therebetween, the middle portion having a cancellous thread for secure engagement with the bone in the two adjacent vertebrae, and a screwdriver for engaging the slotted head for rotating the fastener for threadably engaging an inner surface of one of the channels drilled in the bone and one of the threaded recesses in the cylindrically shaped member.

14. An artificial intervertebral disk system as recited in claim 13 and further including a plurality of washers for lockable communication between the threaded fasteners and the cylindrically shaped member, each washer having a first end with a flat surface for coplanar engagement with a transverse surface of one of the threaded fasteners and a second end with an arcuate shaped surface for continuous lockable engagement with an outer periphery of one of the cylindrically shaped members.

15. An artificial intervertebral disk system as recited in claim 13 wherein the machine thread and the cancellous thread on the middle portion have the same pitch.

16. An artificial intervertebral disk system as recited in claim 1 wherein the paired cylindrically shaped members in the vertical, stacked relationship have their respective cylinders reversed in relation to each other, the spherical ball depending downwardly from the downwardly depending stem and the spherical socket depending upwardly from the upwardly depending stem.

17. An artificial intervertebral disk system as recited in claim 1 wherein the arcuate plates further include a section surrounding each one of the apertures on an outer surface for urging the slotted head of the fastener to a final co-aligned position with the outer surface of the arcuate plates.

18. An artificial intervertebral disk system as recited in claim 1 wherein the paired cylindrically shaped members, the arcuate plates, the fasteners, and the washers all have a surface shaped to encourage adherence to the surrounding vertebral bone.

19. An artificial intervertebral disk system as recited in claim 1 wherein the second fixture means further includes a flat plate having a first side adapted with mini-spikes for temporary securement to the adjacent vertebrae and a second side having a plurality of parallel disposed channels and further having a plurality of positioners for maintaining a space between the adjacent vertebrae, the second side also having a upper end and a lower end adapted for adjustably limiting the length of the cavity and a router bit aperture therebetween adapted for slidable engagement with the parallel disposed channels.

20. A method of replacing a damaged human disk between two adjacent vertebrae in a spinal column with an artificial intervertebral disk for preserving the full range of motion and functionality of the spinal column comprising the steps of:

exposing the anterior portion of the spinal column and removing the damaged disk from between the two adjacent vertebrae;

attaching a routing guide to the adjacent vertebrae;

routing out a cavity in the two adjacent vertebrae to a size sufficient to accept the artificial disk;

removing the routing guide;

implanting the artificial disk in the cavity;

fixturing the artificial disk in a steady, motionless state with the alignment and holding tool;

drilling a plurality of channels through the bone in the two adjacent vertebrae with a stop on the drill bit at about between 10 to 20 millimeters in depth;

measuring the depth of each channel drilled through the bone with a depth gage and selecting the proper length fastener to threadably engage the interior surface of each channel and one of the recesses in the cylindrically shaped member;

packing the cavity with a cortico cancellous bone graft;

removing the alignment and holding tool;

attaching one of the arcuate plates to the cylindrically shaped members and threadably engaging the interior surface of each one of the channels through one of the apertures in the arcuate plates with one of the fasteners;

rotating each fastener with a screwdriver to threadably engage one of the recesses in the cylindrically shaped member; and closing up the anterior portion of the spinal column.

* * * * *